United States Patent
Kim et al.

(10) Patent No.: US 8,343,943 B2
(45) Date of Patent: Jan. 1, 2013

(54) CANCER SENSITIZER COMPRISING GLUCOSAMINE, GLUCOSAMINE DERIVATIVES OR SALTS THEREOF

(75) Inventors: Soo Youl Kim, Seoul (KR); Dae Seok Kim, Seoul (KR)

(73) Assignee: National Cancer Center, Goyang-Si (KR)

( * ) Notice: Subject to any disclaimer, the term of this patent is extended or adjusted under 35 U.S.C. 154(b) by 241 days.

(21) Appl. No.: 12/438,914

(22) PCT Filed: Dec. 6, 2006

(86) PCT No.: PCT/KR2006/005229
§ 371 (c)(1),
(2), (4) Date: Apr. 7, 2009

(87) PCT Pub. No.: WO2007/145405
PCT Pub. Date: Dec. 21, 2007

(65) Prior Publication Data
US 2010/0016249 A1 Jan. 21, 2010

(30) Foreign Application Priority Data

Jun. 16, 2006 (KR) .................. 10-2006-0054519
Nov. 30, 2006 (KR) .................. 10-2006-0119620

(51) Int. Cl.
*A01N 43/04* (2006.01)
*A01N 43/16* (2006.01)
*A61K 31/70* (2006.01)
*A61K 31/35* (2006.01)
*C07D 315/00* (2006.01)

(52) U.S. Cl. ............ 514/62; 514/34; 514/460; 549/417
(58) Field of Classification Search ................. 514/62, 514/460; 549/417
See application file for complete search history.

(56) References Cited

U.S. PATENT DOCUMENTS
4,216,208 A 8/1980 De Barbieri

FOREIGN PATENT DOCUMENTS

| EP | 1666046 A1 | 6/2006 |
|---|---|---|
| KR | 101996001689 | 6/1996 |
| KR | 1020050092783 | 9/2005 |
| KR | 102006008155 | 1/2006 |
| RU | 2138257 C1 | 9/1999 |
| WO | WO-9513061 | 5/1995 |
| WO | WO9513061 A1 * | 5/1995 |
| WO | WO-0238177 | 5/2002 |
| WO | WO 02/080934 A1 * | 10/2002 |
| WO | WO 02/080934 A1 | 10/2002 |
| WO | WO 2007/026996 A1 | 3/2007 |

OTHER PUBLICATIONS

Wolfrom, M. L.; Gibbons, R. A.; Huggard, A. J.,Journal of the American Chemical Society (1957), 79, 5043-6.*
Gennaro, A. R., Remington: The Science and Practice of Pharmacy, 19th edition, 1995, Mack Publishing Company, 3 pages.*
Budavari et al., The Merck Index, 1996, $12^{th}$ edition, published by Merck Research Laboratories, 3 pages.*
Nakanishi et al., Nature Review, 2005, 5, 297-309+2pps.*
Gouze et al., FEBS Letters, 2002, 510, 166-170.*
"Cancer treatment", Merck Manual Online Edition, [retrieved on Feb. 21, 2011]. Retrieved from the Internet http://www.merckmanuals.com/. Revision Aug. 2007.*
O'Neil, Maryadele J., et al. (Editors), The Merck Index 13th Edition, pp. 793-794, 2001.
Office Action issued May 10, 2010 in corresponding Australian application No. 2006344575.
Duffes C. et al., "Anticancer Drug Delivery with Transferrin Targeted Polymeric Chitosan Vesicles" Pharmaceutical Research, 2004, pp. 101-107, vol. 21, No. 1.
Bekesi, J. George et al., "Inhibitory Effect of D-Glucosamine and Other Sugar Analogs on the Viability and Transplantability of Ascites Tumor Cells", Cancer Research, vol. 29, Feb. 1969, pp. 353-359, XP-002591789.
European Search Report for European Application No. 06823936.7 dated Sep. 29, 2010.
Friedman, Susan J. et al., "Membrane-active drugs potentiate the killing of tumor cells by D-glucosamine", Proc. Natl. Acad. Sci USA, Medical Sciences, vol. 77, No. 2, Feb. 1980, pp. 1172-1176, XP-002601076.
Office Action issued on Sep. 14, 2010 for Russian Application No. 2009109248.
Canadian Office Action, dated Nov. 10, 2010, for Canadian Application No. 2,663,398.
Holstege et al., "Effects of D-glucosamine and 6-azauridine on nucleotide contents, 5-fluorouridine uptake, and cytotoxicity in TA3 mammary tumor cells", J Natl Cancer Inst., vol. 76, No. 3, abstract only, Mar. 1986.
European Office Action, dated Sep. 8, 2011, for European Application No. 06823936.7.
Koisumi et al., "HCC Chemo-resistance to Camptothecin Is through NF-κB-Independent Pathway," AASLD Abstracts, Gastroenterology, vol. 124, No. 4, Apr. 1, 2003, pp. A-716 (Abstract only), XP-55005901.
Ozben, "Mechanisms and strategies to overcome multiple drug resistance in cancer," FEBS Letters, vol. 580, No. 12, May 22, 2006, pp. 2903-2909, XP-025171193.

* cited by examiner

*Primary Examiner* — Eric S Olson
*Assistant Examiner* — Zhengfu Wang
(74) *Attorney, Agent, or Firm* — Birch, Stewart, Kolasch & Birch, LLP

(57) ABSTRACT

Disclosed herein is a cancer sensitizer comprising glucosamine, a glucosamine derivative, or a salt thereof. When administered to patients with cancer, the cancer sensitizer functions to sensitize cancer cells to anticancer agents without producing side effects, thereby increasing the therapeutic efficiency of chemotherapy.

6 Claims, 3 Drawing Sheets

CANCER SENSITIZER COMPRISING GLUCOSAMINE, GLUCOSAMINE DERIVATIVES OR SALTS THEREOF

This application is the National Phase of PCT/KR2006/005229 filed on Dec. 6, 2006, which claims priority under 35 U.S.C. 119(a) to Patent Application Nos. 10-2006-0054519 and 10-2006-0119620 filed in Republic of Korea on Jun. 16, 2006 and Nov. 30, 2006, respectively. All of the above applications are hereby expressly incorporated by reference into the present application.

TECHNICAL FIELD

The present invention relates to a cancer sensitizer comprising glucosamine, a glucosamine derivative, or a salt thereof and, more particularly, to the use of glucosamine, a glucosamine derivative or a salt thereof as a cancer sensitizer which can make cancer cells sensitive to anticancer agents and decrease the resistance of cancer cells to anticancer agents, thereby increasing the therapeutic effect of anticancer agents.

BACKGROUND ART

Despite the large number thereof, anticancer agents developed thus far can cure only a few cancers completely. The reason why most cancers cannot be cured completely is that cancer is resistant to anticancer agents, or that tumors are reduced in size in the early stages of chemotherapy, but becomes resistant to anticancer agents during or after chemotherapy. In order to effectively treat cancer with anticancer agents, therefore, chemo-resistance, that is, the resistance of cancer cells to chemicals, must be overcome.

Glucosamine is a major component of chitin, a structural polysaccharide found in large quantities in the exoskeletons of crustaceans, such as shells of marine crabs and shrimps, and safe for the body. Thus, the use of glucosamine in cosmetic compositions (Korean Pat. Application No. 10-2005-7014642) and for the development of arthritis therapeutics (Korean Pat. Application Nos. 10-2005-009182 and 10-2004-0057849) has been attempted. However, it is disclosed in the present invention for the first time that when anticancer agents are administered together with glucosamine, cancer cells are increased in sensitivity to anticancer agents, and thus glucosamine can be used as a cancer sensitizer.

Leading to the present invention, intensive and thorough research into effective chemotherapy, conducted by the present inventors, resulted in the finding that glucosamine or derivatives thereof can reduce the chemo-resistance of cancer cells.

DISCLOSURE OF THE INVENTION

It is therefore an object of the present invention to provide a cancer sensitizer comprising glucosamine, a derivative thereof, or a salt thereof.

It is another object of the present invention to provide a method for disrupting the chemo-resistance of cancer cells, comprising the administration of glucosamine, a glucosamine derivative, or a salt thereof.

It is a further object of the present invention to provide a composition for inhibiting the chemo-resistance of cancer cells, comprising glucosamine, a glucosamine derivative, or a salt thereof in combination with a pharmaceutically acceptable carrier.

It is still a further object of the present invention to provide an anticancer composition, capable of inhibiting the chemo-resistance of cancer cells, comprising the chemo-resistant composition and at least one anticancer agent.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
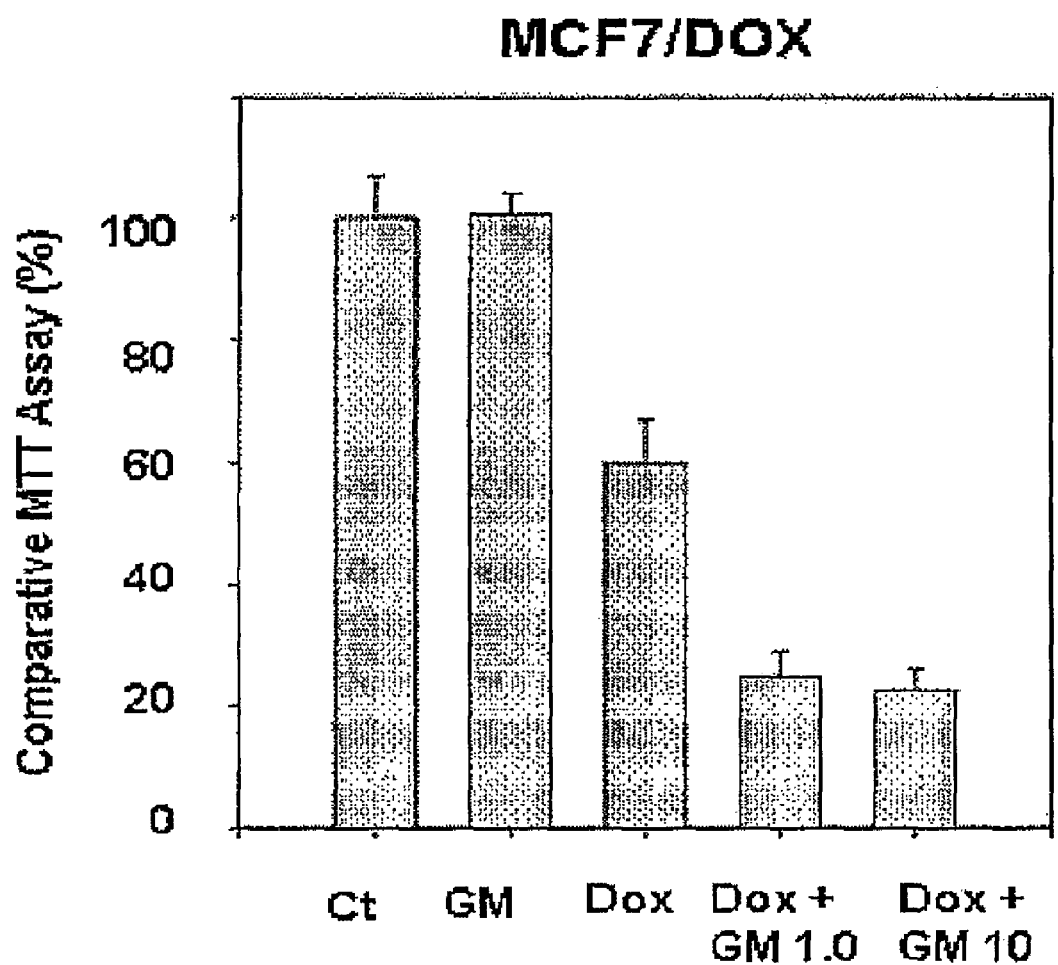
FIG. 1 is a graph showing the cytotoxicity of an anticancer agent on the chemoresistant cell line MCF/DOX in the presence of glucosamine.

In accordance with an aspect thereof, the present invention pertains to a cancer sensitizer comprising glucosamine, a glucosamine derivative, or a salt thereof.

As used herein, the term "cancer sensitization" is intended to have the same meaning as "chemical sensitization", including the effect of, upon chemotherapy, improving or increasing the cytotoxicity of the anticancer agents on cancer cells in the presence of, rather than the absence of, a cancer sensitizer, that is, the effect of decreasing the resistance of anticancer cells to chemicals, such as chemo-resistance, with the aid of a cancer sensitizer to increase the therapeutic effect of the anticancer agents. In the present invention, glucosamine or glucosamine derivatives function to make cancer cells sensitive to anticancer agents and decrease the resistance of cancer cells to anticancer agents, thereby increasing the therapeutic effect of anticancer agents. Therefore, the term "cancer sensitization" is used herein to have the meaning equivalent to "chemical sensitization."

By the term "chemoresistance," as used herein, it is meant that anticancer drugs, when administered, cannot kill cancer cells at all, or can regulate cancer cells only to a slight extent mainly due to the resistance of cancer cells to chemical drugs. On the whole, the term "resistance to chemical drugs" is intended to mean that when cancer patients are treated with anticancer drugs, there are no therapeutic effects, or the therapeutic effect of the anticancer drugs, although high in the early stages of chemotherapy, is progressively attenuated with continual treatment. It is well known in the art that the therapeutic effect of anticancer drugs is gradually decreased with the increasing number of administrations thereof. Chemoresistance is attributed to the appearance of drug-resistant cells.

Glucosamine is a major component of chitin, a structural polysaccharide found in large quantities in the exoskeletons of crustaceans, such as shells of marine crabs and shrimps. Together with chitin, chitosan is a major structural constituent of the exoskeletons. Chitin is a polymer consisting of 2-acetamido-2-deoxy-β-D-glucose (N-acetylglucosamine) and chitosan is poly(β-(1,4)-glucosamine), a polysaccharide obtainable through the deacetylation of chitin. Glucosamine has the structure represented by the following Chemical Formula 1.

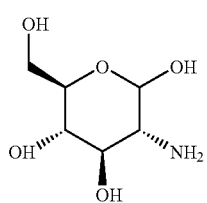

Chemical Formula 1

As used herein, the term "glucosamine derivative" is intended to refer to a glucosamine having an acyl or alkyl moiety substituted for the hydrogen of a hydroxyl group, as represented by the following Chemical Formula 2.

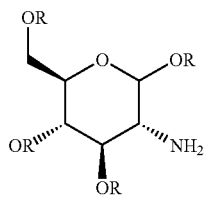

Chemical Formula 2 wherein, R is C2-C18 acyl, or straight or branched C1-C5 alkyl. Preferably, R is selected from an acyl group, consisting of acetyl, propionyl, butyryl, pentanoyl, hexanoyl, heptanoyl, octanoyl, nonanoyl, decanoyl, undecanoyl, lauryl, tridecanoyl, myristyl, pentadecanoyl, palmitoyl, margaryl and stearyl, or from an alkyl group, consisting of methyl, ethyl, propyl, butyl, pentyl, isopropyl, isobutyl and sec-butyl.

As described above, the introduction of hydrophobic groups into the alcohol groups of glucosamine at positions 1, 3, 4, and 6 without change in the amine group, which is believed to be responsible for the physiological activity of glucosamine, results in glucosamine derivatives which naturally decompose well, are non-toxic, highly adsorptive of heavy metals, and highly inhibitory of bacteria, while retaining their intrinsic physiological activity.

Figure 2:
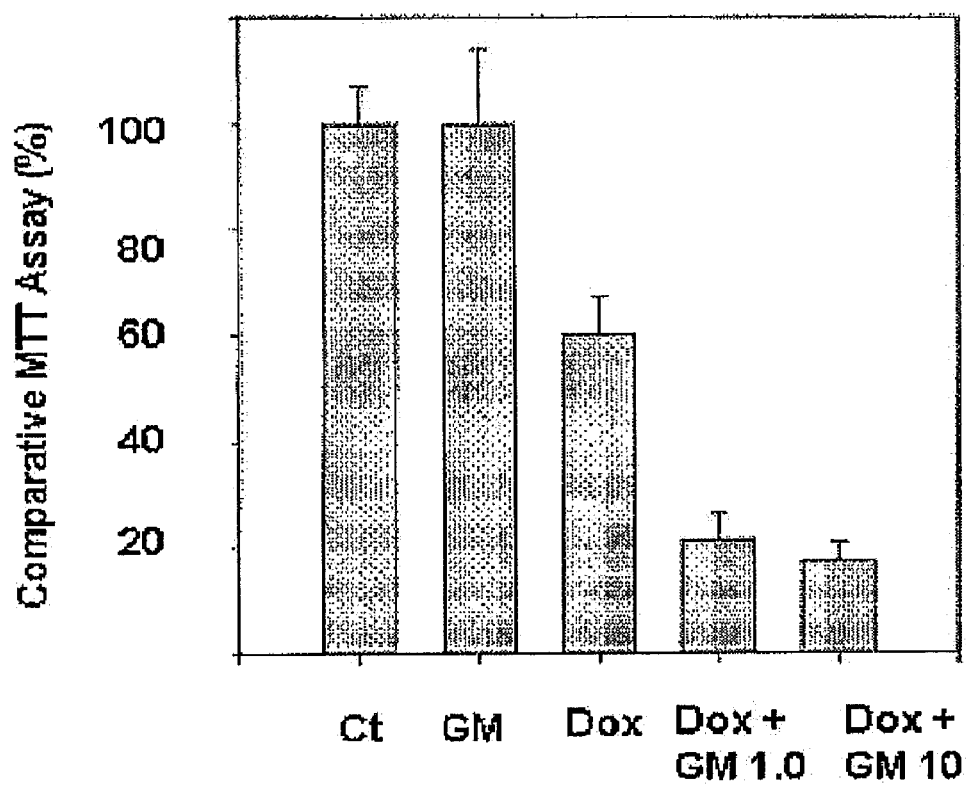
FIG. 2 is a graph showing the cytotoxicity of an anticancer agent on the chemoresistant cell line MDA231 in the presence of glucosamine.

It is found that when an anticancer agent is administered in combination with glucosamine, cancer cells which show chemoresistance are induced to undergo apoptosis twice as frequently as when it is administered alone, as seen in FIGS. 1 and 2. These results demonstrate that glucosamine and derivatives thereof effect cancer sensitization.

Unclear as it is, the cancer sensitization mechanism of glucosamine and derivatives thereof is presumably attributable to inhibitory activity against an enzyme or enzymes playing a critical role in aggravating cancers. That is, it is believed that glucosamine or derivatives thereof inhibit the enzymatic activity responsible for the malignancy of cancer to reduce factors accounting for chemoresistance, thereby making cancer cells sensitive to anticancer drugs.

No particular limitations are imposed on the kind of cancers for which glucosamine or glucosamine derivatives can be used as a cancer sensitizer. That is, glucosamine or glucosamine derivatives can be effectively applied for the treatment of cancer irrespective of the kind of cancer. Therefore, the kind of cancer to which the composition comprising an anticancer drug and glucosamine or a derivative or salt thereof in accordance with the present invention can be applied is dependent on the anticancer drug. For example, glucosamine, glucosamine derivatives or salts thereof may be used as a cancer sensitizer in combination with cisplatin for the treatment of testicular cancer, ovarian cancer, lung cancer, head and neck cancer, cervical spinal cord tumor, neuroblastoma, osteosarcoma, etc., in combination with doxorubicin for the treatment of breast cancer, endometrial cancer, head and neck cancer, Ewing's sarcoma, osteosarcoma, leukemia, etc., in combination with etoposide for the treatment of lung cancer, testicular cancer, osteosarcoma, leukemia, neuroblastoma, etc.

In the composition of the present invention, glucosamine or glucosamine derivatives may be in the form of pharmaceutically acceptable salts. Examples of the pharmaceutically acceptable salts useful in the present invention include sulfates, hydrochlorates, acetates, citrates, and maleates of glucosamine or glucosamine derivatives, but are not limited thereto. Preferable are sulfates of glucosamine or glucosamine derivatives.

In an additional embodiment of the present invention, the composition may further comprise an antioxidant for maintaining the stability of the pharmaceutically acceptable salts of glucosamine or glucosamine derivatives and for preventing the oxidation of the amino group, or a pharmaceutically acceptable metal salt, preferably a sodium or potassium salt of glucosamine or glucosamine derivatives.

In accordance with another aspect thereof, the present invention pertains to a pharmaceutical composition for inhibiting chemoresistance (enhancing chemical sensitization), comprising glucosamine, a glucosamine derivative or a salt thereof, and a pharmaceutically acceptable carrier. This composition may be formulated, together with a carrier, into dosage forms. Examples of the oral dosage forms suitable for the pharmaceutical composition of the present invention include tablets, troches, lozenges, aqueous or emulsified suspensions, powder, granules, emulsions, hard or soft capsules, syrups, and elixirs, but are not limited thereto. Useful for the preparation of tablets or capsules of the pharmaceutical composition according to the present invention are a binder, such as lactose, saccharose, sorbitol, mannitol, starch, amylopectin, cellulose or gelatin, an expedient, such as dicalcium phosphate, a disintegrant, such as corn starch or sweet potato starch, and a lubricant, such as magnesium stearate, calcium stearate, sodium stearyl fumarate or polyethylene glycol wax, alone or in combination. For capsules, a liquid carrier, such as a lipid, may be further used in addition to the above-mentioned compounds.

For non-oral administration, the pharmaceutical composition comprising glucosamine or glucosamine derivatives according to the present invention may be formulated into injections for intravenous or intramuscular routes, suppositories, or sprays inhalable via the respiratory tract, such as aerosols. Injection preparations may be obtained by dissolving or suspending glucosamine or a derivative thereof, together with a stabilizer or a buffer, in water and packaging the solution or suspension in ampules or vial units. Suppositories are typically made of a suppository base, such as cocoa butter or another glyceride, or a therapeutic laxative in which the active substance, that is, glucosamine or a derivative thereof, is diluted. For sprays, such as aerosol, a propellant for spraying a water-dispersed concentrate or wetting powder may be used in combination with an additive.

In accordance with a further aspect thereof, the present invention pertains to an anticancer composition comprising an anticancer agent and the pharmaceutical composition. The term "anticancer agent" or "anticancer drug," as used herein, is intended to refer to a chemical that can kill cancer cells. Most anticancer agents or drugs play a critical role in blocking the replication, transcription and/or translation of DNA in cancer cells. The kind of anticancer agent or drug that can be used in the composition of the present invention is not particularly limited. Anticancer agents or drugs may be selected under standard considerations, such as the kind of cancer cells, the absorption rate of the drug (treatment time period and administration route), the position and size of tumors, etc. For instance, anticancer agents useful in the present invention may be DNA alkylating agents, such as mechlorethamine, chlorambucil, phenylalanine, mustard, cyclophosphamide, ifosfamide, carmustine (BCNU), lomustine (CCNU), streptozotocin, busulfan, thiotepa, cisplatin, and carboplatin. Anticancer antibiotics are also used in the present invention, exemplified by dactinomycin (actinomycin D), doxorubicin, mitoxantrone, plicamycin, mitomycin and C bleomycin. Examples of plant alkaloids as anticancer agents or drugs useful in the present invention include vincristine, vinblastine, paclitaxel, docetaxel, etoposide, teniposide, topotecan and irinotecan. However, anticancer agents or drugs useful in the present invention are not limited to the aforementioned compounds.

In accordance with still another aspect thereof, the present invention pertains to a method for increasing the sensitivity of cancer cells to anticancer drugs through the administration of a cancer sensitizer comprising glucosamine, a glucosamine derivative or a salt thereof.

The term "administration," as used herein, is intended to refer to the introduction of the cancer sensitizer of the present invention into cancer patients in a suitable manner. As long as it leads the cancer sensitizer to a desired tissue, any administration route may be adopted. For example, the administration of the cancer sensitizer may use oral, intraperitoneal, intravenous, intramuscular, intracutaneous, subcutaneous, intranasal, intrapulmonary, intrarectal, intrathecal, and/or intradural routes, but is not limited thereto. The cancer sensitizer according to the present invention may be administered simultaneously with or separately from an anticancer agent or drug. In the latter case, the cancer sensitizer may be administered at predetermined time intervals before or after the administration of an anticancer agent. Preferably, the cancer sensitizer may be administered after anticancer agents. The cancer sensitizer of the present invention may be administered once a day or two or three times a day at predetermined intervals.

In consideration of various factors including the kind of cancer, administration routes, therapeutic effects and chemical sensitization, the cancer sensitizer or the anticancer composition according to the present invention may be suitably administered.

A better understanding of the present invention may be obtained through the following examples, which are set forth to illustrate, but are not to be construed as the limit of the present invention.

Example 1

Preparation of Cells Resistant to Anticancer Drug and Culture Thereof

Human breast cancer cell line MDA-231 (doxorubicin resistant) was purchased from ATCC. MCF-7/DOX (doxorubicin resistant) was obtained from Dr. Kenneth H. Cowan (University of Nebraska Medical Center, 986805 Nebraska Medical Center, Omaha, Nebr. 68198-6805, USA). These cell lines were maintained in media supplemented with 10% fetal bovine serum (Gibco BRL), 1 mM sodium pyruvate (Gibco BRL), and 100 U/ml penicillin-streptomycin (Gibco BRL) at 37° C. in a humid 5% $CO_2$ atmosphere and subcultured every two or three days.

Example 2

Cytotoxicity Assay

An MTT assay was conducted through calorimetric analysis on the reduction of yellow tetrazolium salt into purple formazan in the mitochondria of viable cells. Cells were seeded at a population of $1\times10^5$ cells/well in 24-well plates. After incubation for 24 hrs, the cells were exposed to doxorubicin. This anticancer agent was administered at a dose of 90 μM to MCF 7/DOX and 5 μM to MDA 231. A control was not treated with doxorubicin. On the very day of analysis, the culture medium in each well was substituted with a fresh medium containing MTT (3-(4,5-dimethylthiazol-2-yl)-2,5-diphenyltetrazolium) (Sigma) at a concentration of 0.5 mg per ml, followed by incubation therein for an additional 4 hrs. After the removal of the medium, 500 μl of DMSO was added to each well and the formazan crystals were dissolved using an orbital shaker. Cell viability was represented as a percentage of a test group to the control. These experiments were done in triplicate and repeated at least three times. For each experiment, the mean of three independent experiments and the standard deviations are given.

Example 3

Effect of Glucosamine on Anticancer Agent Sensitivity

MTT assay was conducted to examine whether glucosamine increases the sensitivity of breast cancer cells to anticancer agents. MCF 7/DOX and MDA 231 cell lines, both resistant to anticancer agents, were treated with doxorubicin and glucosamine (1.0 to 10 mM) for 24 hrs. Controls were not treated with glucosamine, while doxorubicin was administered at concentrations of 5 μM to MDA-MB 231, and at a concentration of 90 μM to MCF-7/DOX.

As measured through an MTT assay, almost all MCF 7 and MDA 468, both sensitive to anticancer agent, died, whereas apoptosis took place in about 50% of the anticancer agent-resistant cell lines. When treated with glucosamine, MCF 7/DOX and MDA 231 cell lines became twice as (two times more=three times as) sensitive to doxorubicin than when not treated with glucosamine.

Example 4

Effect of Glucosamine on NF-κB Activity and I-κBα

MCF7/DOX and MDA231 cell lines were cultured in media supplemented with 10% fetal bovine serum (Gibco BRL), 1 mM sodium pyruvate (Gibco BRL) and 100 U/ml penicillin-streptomycin (Gibco BRL) at 37° C. in a humid 5% $CO_2$ atmosphere. A pNF-κB-SEAP vector was transfected into the cells. 24 hrs after transfection, the cells were cultured in the presence of or absence of glucosamine (represented by GM, 5 mM) for 24 hrs. The cell culture was subjected to an SEAP assay, and the cells, after being harvested, were subjected to a β-galactosidase assay. The values obtained for the SEAP assay were corrected for transfection efficiency with a pGAL plasmid (1 μg). β-Galactosidase activity was measured to correct the SEAP activity. The SEAP assay was conducted according to the procedure set forth by the manufacturer (BD Biosciences Clontech, Co.). MCF7/DOX and MDA231 were found to have high expression rates of TGase 2. These assay results are shown in FIG. 3A. These experiments were done in triplicate and repeated at least three times. The values of each experiment are the mean of three independent experiments and the standard deviations.

Glucosamine was analyzed for its effect on I-κBα degradation. For this, MCF7/DOX and MDA231 cells were cultured for 1 hr and cytoplasm fractions thereof were harvested for Western blotting against I-κBα. Western blotting results are shown in the upper panel of FIG. 3B. Western blotting was quantified using a densitometer, and the results are depicted in the lower panel of FIG. 3B. For each value, the mean of three independent experiments and standard deviations are given.

Figure 3:
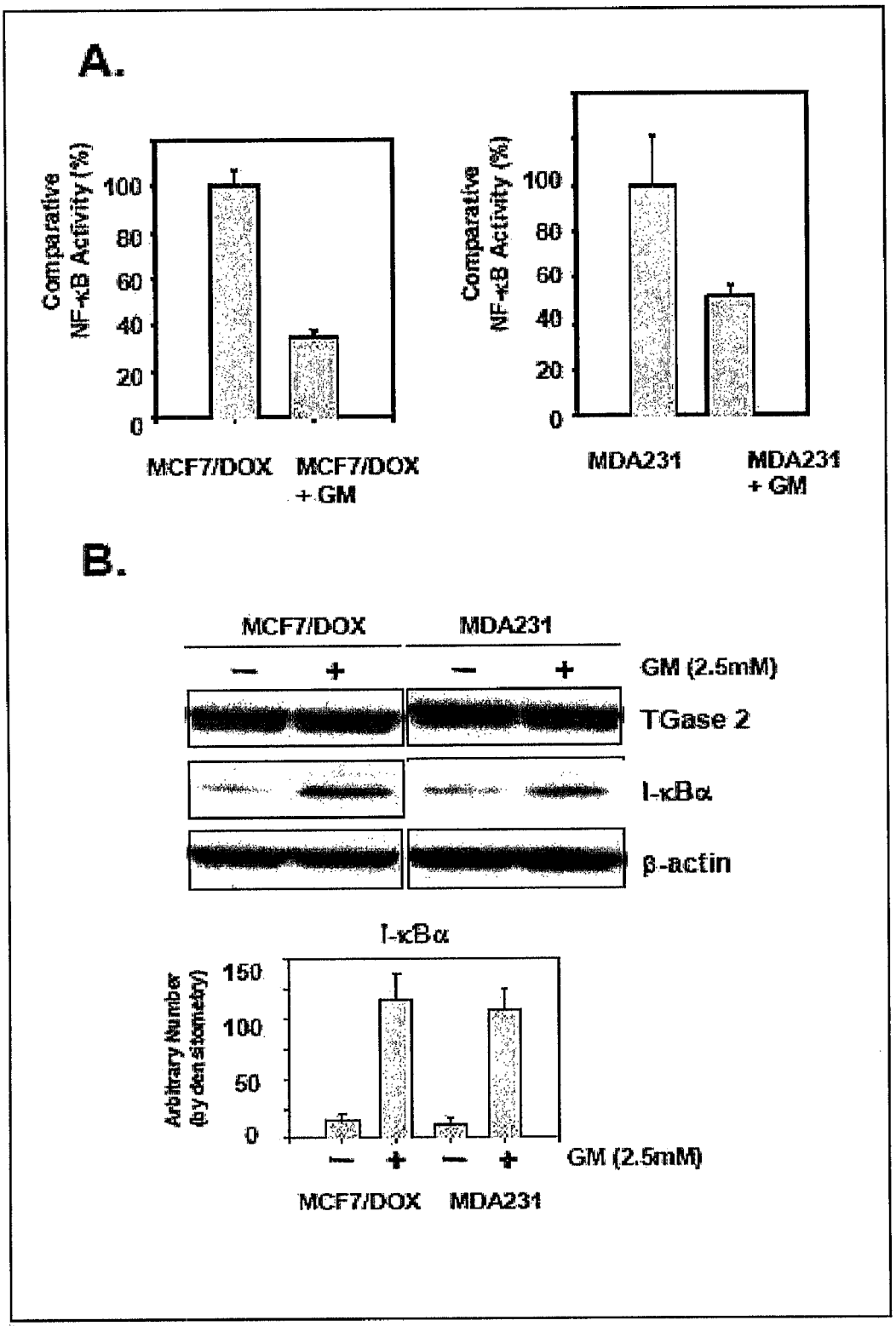
FIG. 3 shows the effect of glucosamine on NF-κB activity and I-κBα degradation in MCF7/DOX and MDA231 cells.

The administration of glucosamine, as understood from the data of FIG. 3, causes the human breast cancer cell lines (MDA-231, MCF-7/DOX) to decrease in NF-κB activity and increase in I-κBα level, which indicates that chemoresistant cell lines sensitively respond to anticancer agents to the point of death, as glucosamine induces a reduction in NF-κB activity (FIGS. 2 and 3).

INDUSTRIAL APPLICABILITY

As described hitherto, glucosamine, a naturally occurring, harmless material, or glucosamine derivatives can be used as a cancer sensitizer which makes cancer cells highly sensitive to anticancer agents without the production of particular side effects, in contrast to conventional chemical sensitizers.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for increasing sensitivity and decreasing resistance of breast cancer cells to chemotherapy, comprising:
administering an anticancer agent and glucosamine, a glucosamine derivative or a salt thereof as a cancer sensitizer, simultaneously with or sequentially with said anticancer agent, to a subject having breast cancer and having resistance to the anticancer agent, wherein the method reduces a NF-κB activity and increases a I-κBα level in the subject.

2. The method according to claim 1, wherein the salt is a sulfate.

3. The method according to claim 1, wherein the glucosamine derivative is represented by the following formula:

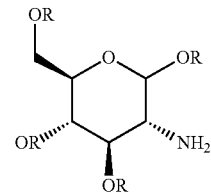

wherein, R is an acyl group having 2 to 18 carbon atoms or a straight or branched alkyl group having 1 to 5 carbon atoms.

4. The method according to claim 1, wherein said anticancer agent is at least one selected from the group consisting of mechlorethamine, chlorambucil, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin, C bleomycin, vincristine, vinblastine, paclitaxel, docetaxel, etoposide, teniposide, topotecan and irinotecan.

5. The method according to claim 1, wherein said cancer sensitizer is administered simultaneously with said anticancer agent.

6. The method according to claim 1, wherein said cancer sensitizer is administered after said anticancer agent.

* * * * *